(12) United States Patent
Kurata (10) Patent No.: US 7,563,940 B2
(45) Date of Patent: Jul. 21, 2009

(54) WOUND DRESSING AND WOUND DRESSING KIT

(75) Inventor: Shuhei Kurata, Osaka (JP)

(73) Assignees: Zuiko Corporation, Osaka (JP); Makoto Natsui, Nagano (JP)

( * ) Notice: Subject to any disclaimer, the term of this patent is extended or adjusted under 35 U.S.C. 154(b) by 145 days.

(21) Appl. No.: 11/311,504

(22) Filed: Dec. 19, 2005

(65) Prior Publication Data

US 2006/0094997 A1    May 4, 2006

(30) Foreign Application Priority Data

Jun. 26, 2003   (JP)  ............... 2003-183180
Jan. 22, 2004   (JP)  ............... 2004-014613

(51) Int. Cl.
    *A61F 13/00*   (2006.01)
(52) U.S. Cl. ............... 602/45; 602/41; 602/42; 602/58
(58) Field of Classification Search ............ 602/41–59; 128/888, 889; 604/304–308; 428/136
    See application file for complete search history.

(56) References Cited

U.S. PATENT DOCUMENTS

| | | | | |
|---|---|---|---|---|
| 3,521,631 | A | * | 7/1970 | Rovee et al. ............ 602/42 |
| 3,814,101 | A | * | 6/1974 | Kozak ............ 604/370 |
| 3,888,247 | A |   | 6/1975 | Stenvall |
| 3,890,974 | A | * | 6/1975 | Kozak ............ 604/368 |
| 4,499,896 | A | * | 2/1985 | Heinecke ............ 602/47 |

FOREIGN PATENT DOCUMENTS

| | | |
|---|---|---|
| JP | 06-205825 A | 7/1994 |
| JP | 07-080020 A | 3/1995 |
| JP | 07-136240 A | 5/1995 |
| JP | 08-196613 A | 8/1996 |
| JP | 09-10296 A | 1/1997 |
| JP | 10-151184 A | 6/1998 |
| JP | 11-081116 A | 3/1999 |
| JP | 11-276571 | 10/1999 |
| WO | 01/60296 A1 | 8/2001 |

OTHER PUBLICATIONS

Chinese Office Action for corresponding Application No. 2004800176075 dated April 6, 2007 (English translation provided).
JIS L 1092; "Testing methods for water resistance of textiles"; Japanese Industrial Standard; 1998.
JIS L 1096; "Testing methods for woven fabrics"; Japanese Industrial Standard, 1999.

\* cited by examiner

*Primary Examiner*—Kim M Lewis
(74) *Attorney, Agent, or Firm*—Renner, Otto, Boisselle & Sklar, LLP (57) ABSTRACT

A wound dressing comprises a first layer 10 including a sheet that exerts a water pressure resistant function at an initial stage, a second layer 20 including an absorptive material, and a third layer 30 including a sheet impermeable to liquid. The first layer 10, the second layer 20 and the third layer 30 are integrally stacked together so that the second layer 20 is sandwiched between the first layer 10 and the third layer 30. The wound dressing will not be completely stuck on the wound surface, the exudates can be adequately held on the wound surface, and the exudates can be prevented from leaking to the outside through the dressing.

21 Claims, 5 Drawing Sheets

WOUND DRESSING AND WOUND DRESSING KIT

CROSS-REFERENCE TO RELATED APPLICATIONS

This application is a Continuation of International Application No. PCT/JP2004/008868, filed Jun. 24, 2004, which was not published under PCT Article 21(2) in English. The International Application No. PCT/JP2004/008868 is based upon and claims the benefit of priority from prior Japanese Patent Applications No. 2003-183180, filed Jun. 26, 2003; and No. 2004-014613, filed Jan. 22, 2004, the entire contents of both of which are incorporated herein by reference.

BACKGROUND OF THE INVENTION

The present invention relates to a wound dressing and a wound dressing kit suitable for medical treatment of a wound such as a burn, a decubitus, a contusion, an excoriation and an ulcer.

It has recently been found that a wet environment on a wound surface has a great influence on the wound healing. Particularly, components contained in the exudate from the wound site assist in promoting the wound healing. Based on this point of view, methods have been employed for medical treatment of a wound, in which the wound is not disinfected so as to maintain a wet environment provided by the exudate from the wound, as opposed to medical treatment of a wound by drying the wound surface. For such a medical treatment method, various types of wound dressings (hereinafter referred to simply as "dressings") have been developed.

In order to effectively perform such a wound healing method, a dressing is required to have the following functions and effects.

(i) To adequately hold the exudate, thereby preserving an adequate wet environment of the wound surface.

(ii) To adequately discharge the exudate from the wound, thereby preventing the wound surface from being pressed by the exudate and preventing "undermining" due to excessive exudate (an phenomenon in which the skin of the wound site is dug by the pressure from the exudate).

(iii) To prevent the dressing from being completely stuck on the wound surface.

(iv) To prevent the exudate from leaking to the outside through the dressing.

(v) To allow the dressing to be cut into a piece of any size and shape as intended according to the size and shape of the wound surface.

Japanese Laid-Open Patent Publication No. 6-205825 (1) and Japanese Laid-Open Patent Publication No. 7-80020 (2) each disclose a dressing using a porous film that includes a hydrophilic substance dispersed therein or that is covered with a hydrophilic substance.

Japanese Laid-Open Patent Publication No. 8-196613 (3) and Japanese Laid-Open Patent Publication No. 11-276571 (4) each disclose a dressing using a sponge layer containing N-succinyl-chitosan therein and a reinforcing material (e.g., a non-woven fabric).

Japanese Laid-Open Patent Publication No. 10-151184 (5) discloses a dressing in which a chitin-chitosan cellulose mixed fiber is used on the wound surface.

The first patent document: Japanese Laid-Open Patent Publication No. 06-205625 (abstract)

The second patent document: Japanese Laid-Open Patent Publication No. 07-080020 (0010 and 0011 paragraphs)

The third patent document: Japanese Laid-Open Patent Publication No. 08-196613 (abstract)

The fourth patent document: Japanese Laid-Open Patent Publication No. 11-276571 (abstract)

The fifth patent document: Japanese Laid-Open Patent Publication No. 10-151184 (abstract)

SUMMARY OF THE INVENTION

In the dressings disclosed in the first patent document and the second patent document, a porous film is used to improve the ability to discharge the exudate (wound fluid) from the wound, but the first and second documents fail to take into consideration the adequate holding of the exudate. In the third patent document and the fourth patent document, a moisture-permeable non-woven fabric is used as a reinforcing material to improve the ability to discharge the exudate from the wound, but the third and the fourth patent documents fail to take into consideration the adequate holding of the exudate.

In the fifth patent document, the function of preserving the wet environment of the wound surface and the exudate-absorbing property are improved, but the leakage of the exudate to the outside through the dressing is not improved. Therefore, the dressing of this patent document requires additional use of an anti-leak material such as gauze.

Moreover, it has been indicated that a conventional hydrocolloid dressing being left on a skin for a long period of time will cause a skin redness or a heat rash.

It is therefore an object of the present invention to provide a dressing that solves these problems.

In order to achieve the object set forth above, a dressing of the present invention includes a first layer made of a sheet material that exerts a water pressure resistant function at an initial stage, a second layer made of an absorptive material, and a third layer made of a liquid-impermeable sheet material. This sheet material that exerts the water pressure resistant function at the initial stage is hydrophobic.

A dressing of the present invention is a dressing applied on a wound site so as to cover the wound site, comprising a permeable layer, an absorptive layer and an impermeable layer, the layers being integrally stacked together so that the absorptive layer is sandwiched between the permeable layer and the impermeable layer. The permeable layer exerts a water pressure resistant function at an initial stage. The absorptive layer exerts a function of absorbing an exudate, which has exuded from the wound site and passed through the permeable layer. The impermeable layer is impermeable to liquid (hereinafter expressed as "liquid impermeability"), thereby preventing leakage of the exudate.

In a dressing of the present invention, a contact surface of the first layer or the permeable layer that faces the wound site has a surface configuration with asperity (protrusions/depressions).

In a dressing of the present invention, the first layer or the permeable layer includes a porous sheet, a depth of pores in the porous sheet is set to be about 100 μm to 2000 μm, a pore ratio of the porous sheet is set to be 5% to 50%, and the porous sheet is placed on a contact surface facing the wound site.

A dressing of the present invention includes an absorbent as an absorptive material.

In a dressing of the present invention, a non-woven fabric that has been made into a sheet through interfiber bonding with a binder or compression (e.g., an air-laid pulp) is used as an absorptive material.

With the use of a member that exerts the water pressure resistant function at the initial stage in the first layer, in the initial stage after the dressing is applied on the wound site, the exudate is held on the wound surface by the waterproof effect of the member that exerts the water pressure resistant function at the initial stage, thus forming a closed space, thereby preserving a wet environment therein.

The member that exerts the water pressure resistant function at the initial stage does not have a complete waterproof function, and when the wound surface is filled with the exudate and the pressure in the closed space is increased, the waterproof function of the member decreases, whereby excessive exudate is discharged into, and absorbed by, the second layer. Thus, it is possible to prevent the pressure in the closed space from increasing excessively.

The liquid-impermeable third layer prevents the exudate absorbed by the second layer from leaking to the outside.

Thus, the present invention provides the following effects.

(i) Since the first layer that exerts the water pressure resistant function at the initial stage exerts an adequate (incomplete) waterproofness, the exudate is held on the wound surface while excessive exudate is discharged from the first layer to the second layer, thereby preserving an adequately wet environment of the wound surface. This promotes the wound healing.

(ii) Since the first layer exerts the water pressure resistant function at the initial stage and has protrusions/depressions thereon, the dressing will not be completely stuck on the wound surface, and the dressing can easily be peeled off the wound surface.

(iii) The third layer is capable of preventing the leakage of the exudate to the outside.

(iv) By forming the second layer or the absorptive layer of an air-laid non-woven fabric, it is unlikely that super water-absorbing polymer powder or a fibrous component such as fluff pulp will come off when the dressing is cut into a piece of an appropriate size.

(v) By coloring the third layer, the front and back sides of the dressing can be discerned from each other. Depending on the color to be used, the dressing applied can be made less conspicuous.

(vi) By making the third layer transparent, when to replace the dressing can be appropriately perceived.

(vii) By providing the dressing in a roll form, pieces of dressings can be cut off continuously from the roll with any size and shape as intended according to the size and shape of wound surfaces, thus providing an economical advantage.

(viii) By using, as the first layer or the permeable layer, a sheet material such that the surface area (the contact area with the wound surface) can be kept small, the dressing is unlikely to be stuck on the wound surface even if there is only a small amount of exudate. Moreover, since the dressing is unlikely to be stuck on the wound surface and is capable of absorbing excessive exudate, the dressing is unlikely to cause a skin redness or a heat rash even if it is left on the skin for a long period of time.

BRIEF DESCRIPTION OF THE DRAWINGS

FIGS. 1(*a*) and 1(*b*) are schematic, enlarged sectional views showing a dressing according to an embodiment of the present invention and a dressing according to a variation of the embodiment of the present invention.

FIGS. 2(*a*), 2(*b*) and 2(*c*) are schematic, enlarged sectional views showing other variations.

FIGS. 3(*a*) and 3(*b*) are schematic perspective views each showing a dressing kit of the present invention.

FIGS. 4(*a*), 4(*b*), 4(*c*), 4(*d*) and 4(*e*) are schematic, enlarged sectional views each showing an example of a porous sheet of a dressing of the present invention.

FIGS. 5(*a*) and 5(*b*) are a schematic, enlarged sectional view and an enlarged perspective view showing an example of a sheet material having protruding portions of the present invention, and FIGS. 5(*c*) and 5(*d*) are a schematic, enlarged sectional view and an enlarged perspective view showing an example of a sheet material having depressed portions of the present invention.

DESCRIPTION OF THE REFERENCE NUMERALS

10: First layer (permeable layer)
15: Porous sheet
16: Pores
20: Second layer (absorptive layer)
30: Third layer (impermeable layer)

DESCRIPTION OF THE PREFERRED EMBODIMENTS

An embodiment of the present invention will now be described with reference to the drawings.

Figure 1:
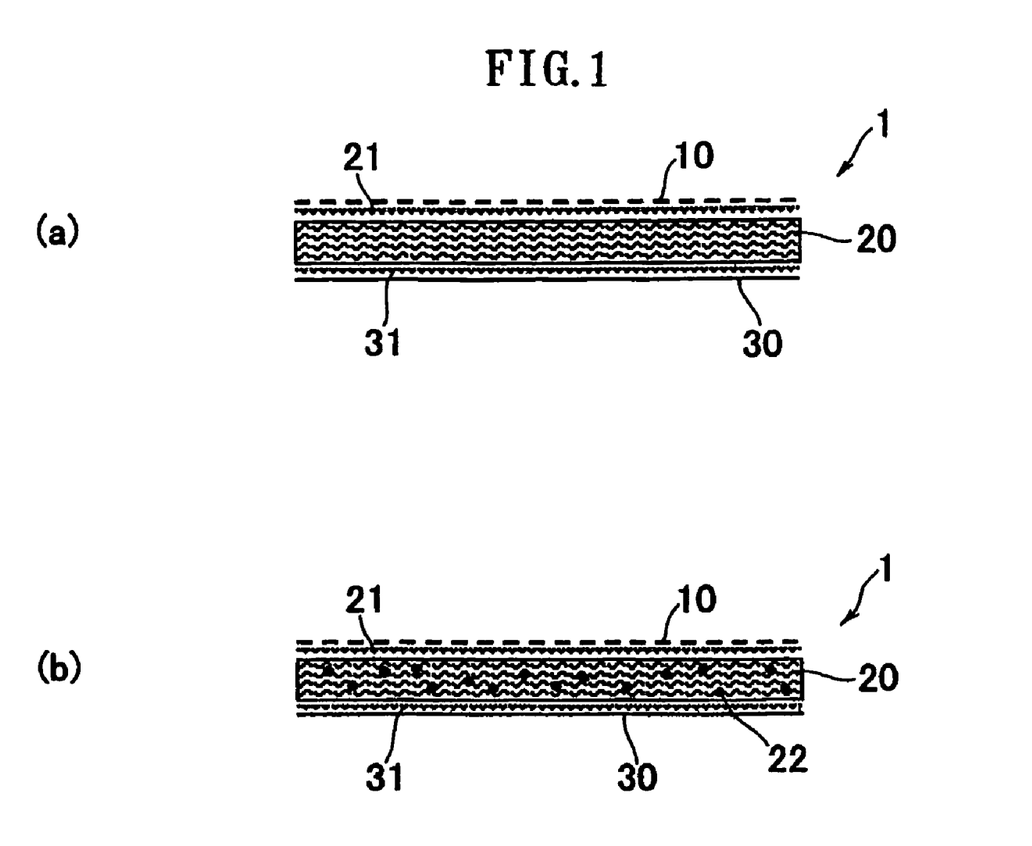

Referring to FIGS. 1(*a*) and 1(*b*), a dressing 1 has three layers including a first layer (permeable layer) 10 to be in face-to-face contact with the wound surface and the skin surface, a second layer (absorptive layer) 20 for absorbing the exudate, and a third layer (impermeable layer) 30 for preventing the leakage of the exudate. It is preferred that the three layers 10, 20 and 30 are bonded together so that they will not peel apart from each other. Methods for bonding the three layers 10, 20 and 30 together include, in addition to bonding with an adhesive agent 21, 31 such as a hot melt adhesive agent, fusion by a heat seal process, and an embossing process.

A water-resistant sheet material that exerts a water pressure resistant function at an initial stage is used as a material of the first layer 10. Such a sheet material may be a non-woven fabric, a microporous film, etc.

As used herein, "exerting a water pressure resistant function at an initial stage" means having a function of withstanding the pressure from the exudate to prevent the exudate from passing therethrough at the initial stage when the exudate starts exuding from the wound, and having a function of allowing the exudate to pass therethrough when the pressure from the exudate exceeds a predetermined value. Thus, a member that exerts the water pressure resistant function at the initial stage has such a degree of water-resistance that it remains water-resistant at the initial stage when there is only a small amount of exudate but that it becomes no longer water-resistant when the amount of exudate increases after a continued use so that the pressure in the closed space (between the first layer 10 and the skin surface) is increased, thereby allowing the exudate to pass therethrough. Such a material that exerts the water pressure resistant function at the initial stage is hydrophobic.

The water pressure resistant function at the initial stage can be represented by the air permeability (JIS L 1096) and the water repellency score (JIS L 1092). In order to exert an appropriate water pressure resistant function at the initial stage, it is necessary that the air permeability is 20 to 2000 [$cm^3/cm^2 \cdot s$] and that the water repellency score is 3 points or more. More preferably, the air permeability is in the range of 80 to 500 [$cm^3/cm^2 \cdot s$].

If the air permeability is less than 20 [$cm^3/cm^2 \cdot s$], the water-resistance of the sheet material will be excessive. Then, even when the amount of exudate in the closed environment increases and thus the pressure therein increases, the exudate is not allowed to pass therethrough into the second layer 20, whereby the exudate will be held within the closed environment with the increased pressure therein. This is undesirable as the exudate presses the wound surface and causes "undermining" of the wound surface. If the air permeability is no less than 2000 [cm$^3$/cm$^2$·s], the water-resistance will be too low, whereby the exudate is entirely allowed to pass therethrough to be absorbed by the second layer 20 from the initial stage. Therefore, it is not possible to keep an optimal wet environment by the exudate for healing the wound.

In contrast, if the air permeability is 20 to 2000 [cm$^3$/cm$^2$·s], it is possible to hold the exudate under an adequate pressure in the closed environment. Therefore, it is possible to prevent the "undermining" of the wound surface while obtaining a desirable water-resistance, thereby maintaining an optimal wet environment by the exudate. Particularly, if the air permeability is 80 to 500 [cm$^3$/cm$^2$·s], it is supposed that it is possible to maintain such an optimal wet environment over a long period of time.

The water repellency score being less than 3 points (i.e., 2 points or less) is undesirable because the water-resistance at the initial stage condition will not be satisfied, and the dressing will be stuck on the wound surface during the medical treatment and cannot easily be peeled off when replacing the dressing with a new dressing. The water-resistance at the initial stage of the dressing and the degree of stickiness thereof are correlative with the surface energy of the first layer. That is, as the first layer has a smaller surface energy, it is more likely that the water-resistance at the initial stage will be satisfied and the sticking will be avoided. The surface energy can be evaluated based on the water repellency score.

Note that the air permeability is measured by Method A (Frazier method) as set forth in 8.27.1 of JIS L 1096. In this measurement method, a Frazier textile air permeability tester is used. Specifically, a test piece is attached to the Frazier tester, and the suction fan is adjusted by using the rheostat so that the inclined barometer shows a pressure of 125 Pa. The air permeability is measured by obtaining the air volume [cm$^3$/cm$^2$·s] passing through the test piece, with reference to a tabular chart accompanying the tester, based on the pressure shown by the upright barometer and the type of air hole used. Note that the air permeability is obtained as the arithmetical mean of five measurements.

On the other hand, the water repellency score (JIS L 1092) is measured by the water repellency test (spray test) as set forth in 6.2 of JIS L 1092. In this measurement method, a water repellency tester having a spray nozzle with a predetermined capability (a capability of spraying 250 ml of water in 25 to 30 seconds) is used. Specifically, the water repellency score is determined by: (1) attaching a test piece measuring approximately 20 cm×20 cm to the test piece holder of the water repellency tester and spraying 250 ml of water through the spray nozzle onto the test piece in 25 to 30 seconds; (2) removing the holder from the stand of the water repellency tester and shaking excessive water drops off the test piece through a predetermined procedure; and then (3) comparing the wet condition of the test piece attached to the holder with those of predetermined wet condition samples. The predetermined procedure in step (2) is to horizontally hold one end of the holder and turn the test piece by 180° with the upper surface of the test piece facing down and with the other end of the holder being gently pressed against a solid object.

Note that the temperature during the water repellency test is controlled at 20±2° C., and the water used in the measurement is distilled or ion-exchanged water.

The wet condition of each sample is as defined below.

1 point: The entire upper surface is wet 2 points: Half of the upper surface is wet with small discrete wet spots penetrating the cloth 3 points: Small discrete droplet-like wet spots are observed on the upper surface 4 points: No wet areas are observed on the upper surface but small water droplets are observed thereon 5 points: No wet areas and no water droplets are observed on the upper surface Therefore, "the water repellency score being 3 points or higher" as used herein includes cases where small discrete droplet-like wet spots are observed on the upper surface, cases where no wet areas are observed on the upper surface but small water droplets are observed thereon and cases where no wet areas and no water droplets are observed on the upper surface, but do not include cases where the entire upper surface is wet or cases where half of the upper surface is wet with small discrete wet spots penetrating the cloth.

Note that the water repellency test of JIS L 1092 as described above is a test method similar to that of ISO 4920.

The sheet material that exerts the water pressure resistant function at the initial stage may be a non-woven fabric or a microporous film made of a hydrophobic material such as a polyolefin resin (polypropylene, polyethylene, etc.), a polyester resin (polyethylene terephthalate, polybutylene terephthalate, polypropylene terephthalate, etc.), polyamide (Nylon 6, Nylon 66, etc.) (registered trademarks), and a polyurethane resin. It is particularly (most) preferred that a non-woven fabric is used for the first layer or the permeable layer 10.

The type of non-woven fabric is not limited to any particular type, and may be a wet-laid or dry-laid non-woven fabric (thermally-bonded, needle-punched, spunlaced, etc.), a spun-bonded non-woven fabric, a meltblown non-woven fabric, a flash-spun non-woven fabric, a composite non-woven fabric thereof (SMS, SMMS, etc.), or the like.

It may alternatively be a non-woven fabric made of a hydrophilic material such as cotton or rayon that has been processed to be water-repellent.

It is particularly preferred that a meltblown non-woven fabric obtained by a meltblown method or a flash-spun non-woven fabric obtained by a flash-spinning method is used for the non-woven fabric contained in the first layer 10 or the permeable layer 10.

A meltblown non-woven fabric or a flash-spun non-woven fabric is formed by extra-fine fibers having a very small diameter (fiber diameter) (e.g., about 20 µm or less). Therefore, for the same weight (grammage), such a non-woven fabric, as compared with a non-woven fabric obtained by other production methods such as the spunbond method, has smaller interstices between fibers and is thus more likely to exert a desirable water pressure resistant function at the initial stage.

Simply stated, a meltblown non-woven fabric is obtained by opening and drawing fibers by discharging a jet of high temperature and pressure air to the outlet of the spinneret, and is formed by continuous extra-fine fibers. Note that the meltblown non-woven fabric may be used in the form of a so-called "SMS non-woven fabric", a so-called "SMMS non-woven fabric", or the like, obtained by layering together a spunbonded non-woven fabric and a meltblown non-woven fabric.

A flash-spun non-woven fabric is a meshed non-woven fabric formed by extra-fine fibers, and is obtained by uniformly dissolving a fiber-forming polymer in a low-boiling solvent under high temperature and pressure, discharging the solvent through nozzles, and rapidly gasifying and expanding only the solvent to thereby cure the fiber-forming polymer being drawn.

Moreover, with a meltblown non-woven fabric and a flash-spun non-woven fabric, which are made of continuous fibers being in a substantially continuous form, it is possible to suppress the fabric from becoming fluffed due to bleeding of ends of fibers on the surface of the fabric and to suppress pieces of the fabric from coming off. Therefore, the fluff, etc., is prevented from being taken by and stuck onto the wound surface (hereinafter referred to as "adhesion") during the epithelization. Therefore, the dressing can be smoothly peeled off the wound surface.

The non-woven fabric included in the first layer 10 or the permeable layer 10 may be calendered. Calendering is a process of pressurizing a non-woven fabric by using a calender roll or an embossing roll whose temperature is adjusted to no more than the melting point. Through such a calendering process, some fibers of the non-woven fabric are thermally fused and interstices formed therebetween are clogged, whereby the non-woven fabric is more likely to exert a desirable water pressure resistant function at the initial stage. Moreover, since the fluffing on the surface of the first layer 10 is suppressed, the adhesion of the non-woven fabric on the wound surface is suppressed.

It is preferred that a sheet material, with which the contact area between the first layer 10 or the permeable layer 10 and the wound surface can be kept small, is placed on the contact surface of the first layer 10 or the permeable layer 10 facing the wound surface. Then, even if there is only a small amount of exudate, the dressing 1 is unlikely to be stuck on the wound surface. The sheet material may be, for example, a sheet material with protrusions/depressions. A sheet material with protrusions/depressions as used herein is a sheet material in which at least the contact surface thereof facing the wound site has an unsmooth surface configuration with a plurality of projections, hollows or pores formed therein. While the protrusions/depressions as used herein are different from fine fluff of a non-woven or woven fabric, the sheet material with protrusions/depressions may be formed by a non-woven fabric, or the like.

The sheet material with protrusions/depressions is preferably a porous sheet 15 with a plurality of pores 16 passing therethrough, as shown in FIGS. 4(a) to 4(e).

Figure 4:
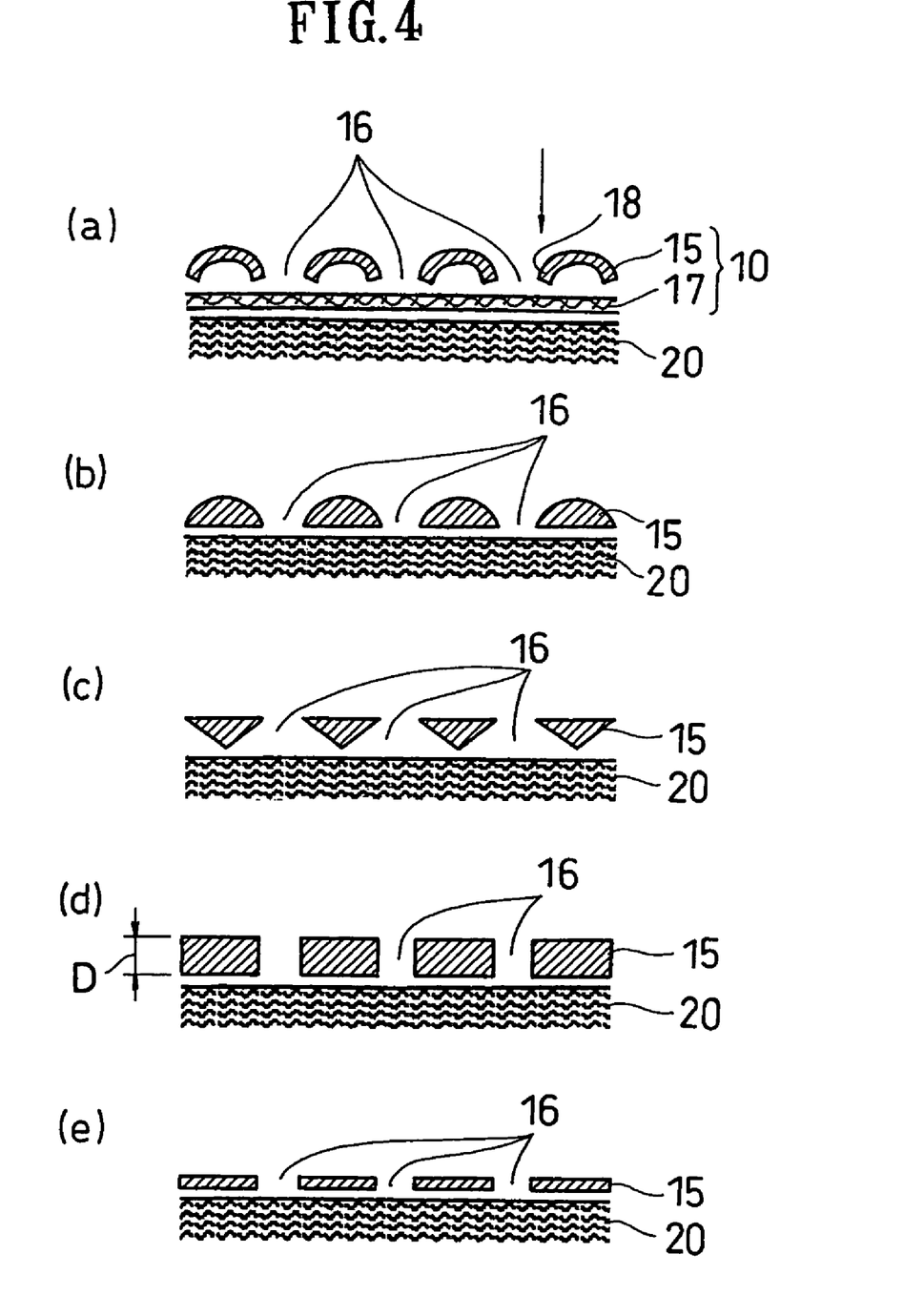

The pore 16 of the porous sheet 15 preferably has a predetermined depth D (FIG. 4(d)). For example, the depth D of the pore 16 may be about 100 µm to 2000 µm. It is supposed that the depth D of the pore 16 may preferably be about 250 µm to 500 µm.

The shape of the pore 16 may be any of those shown in FIGS. 4(a) to 4(e), for example.

In the sheet 15 of FIG. 4(e), although a plurality of pores 16 are formed therein, if the pores 16 are too shallow (i.e., if the depth D is too small), the wound site may be in contact not only with the front surface of the sheet 15 (the surface away from the absorptive layer 20) but also with the absorptive layer 20 on the lower side of the sheet 15. Then, as with an apparently-smooth surface material, the contact area between the wound site and the dressing 1 may increase, whereby the dressing 1 cannot easily be peeled off. In contrast, where the porous sheet 15 has pores 16 therein with a predetermined depth D as those shown in FIGS. 4(a) to 4(d), only the surface portions of the porous sheet 15 will be in contact with the wound site, whereby it is possible to keep the contact area between the wound are and the dressing 1 small. Therefore, the dressing 1 can easily be peeled off.

It is understood that the shape of the pores 16 is not limited to those shown in FIGS. 4(a) to 4(e), but may be any other suitable shape.

Note that the porous sheet can be obtained by, for example, forming pores with any of various methods in a resin sheet with a flat surface. While FIGS. 4(a) to 4(e) schematically show the pores 16 in the porous sheet 15 being arranged regularly, the pores 16 may alternatively be arranged irregularly.

The pore ratio of the porous sheet 15 ((the total area of the pore 16/the area of the porous sheet 15)×100) is preferably 5% to 50%. It is supposed that the pore ratio is more preferably 15% to 40%.

In a case where the pores 16 of the porous sheet 15 are formed in a tubular shape so as to have a predetermined depth D as shown in FIG. 4(a), tubular portions 18 can be compressively deformed in the direction indicated by an arrow when the porous sheet 15 receives a load thereon. Therefore, in the area where the dressing 1 is applied, it is possible to realize a high cushion effect against external stimuli.

If the sheet material with protrusions/depressions exerts the water pressure resistant function at the initial stage, the first layer 10 can be formed by a single sheet material (FIGS. 4(b) to 4(e)). On the other hand, if the sheet material with protrusions/depressions does not exert the water pressure resistant function at the initial stage, the first layer 10 can be formed by a composite sheet of the sheet material with protrusions/depressions and an additional sheet material 17 that exerts the water pressure resistant function at the initial stage as shown in FIG. 4(a). Then, the additional sheet material 17 is placed on a surface that faces the second layer (the absorptive layer) of the sheet material with protrusions/depressions. The first layer 10 may be formed by a composite sheet material of three or more sheet materials by using more additional sheet materials.

FIGS. 5(a) to 5(d) show alternative examples of the sheet material with protrusions/depressions.

Figure 5:
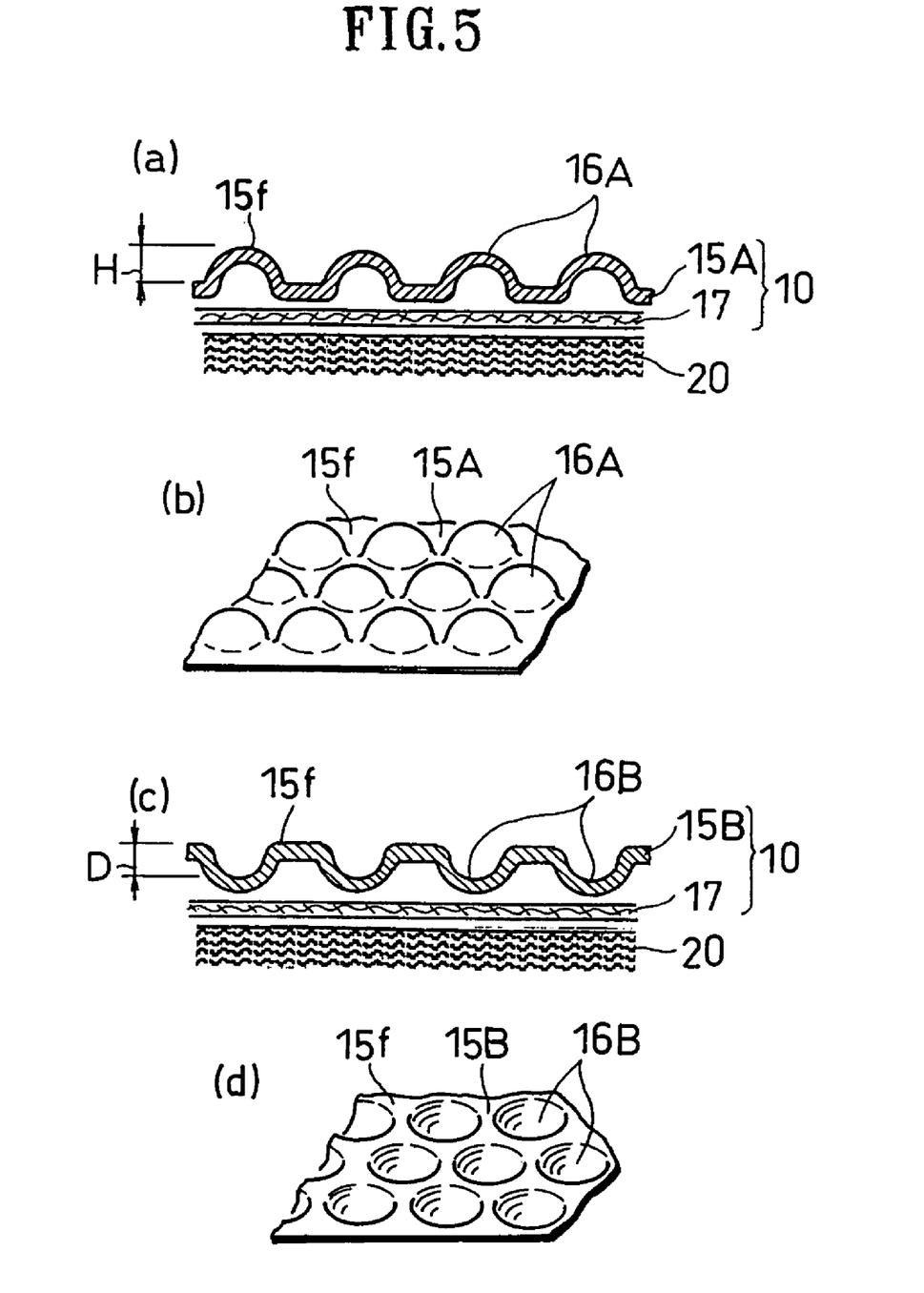

Referring to FIGS. 5(a) and 5(b), a protrusion sheet 15A has many (a plurality of) protruding portions 16A. A surface 15f of the protrusion sheet 15A on which the protruding portions 16A are formed faces the wound surface. Therefore, the protruding portions 16A of the surface 15f primarily contact the wound surface (with portions of the surface 15f other than the protruding portions 16A being spaced apart from the wound surface), whereby the contact area between the surface 15f and the wound surface will be smaller than the surface area of the surface 15f. Note that it is supposed that the height H of the protruding portions 16A is preferably about 100 µm to 2000 µm.

Referring to FIGS. 5(c) and 5(d), a depression sheet 15B has many (a plurality of) depressed portions 16B. The surface 15f of the depression sheet 15B on which the depressed portions 16B are formed faces the wound surface. Therefore, the depressed portions 16B of the surface 15f do not contact the wound surface (with only portions of the surface 15f other than the depressed portions 16B being in close proximity to the wound surface), whereby the contact area between the surface 15f and the wound surface will be smaller than the surface area of the surface 15f. Note that it is supposed that the depth D of the depressed portions 16B is preferably about 100 µm to 2000 µm.

If the sheet materials 15A and 15B with protrusions/depressions exert the water pressure resistant function at the initial stage, the first layer 10 can be formed by a single sheet material. On the other hand, if the sheet materials 15A and 15B with protrusions/depressions do not exert the water pressure resistant function at the initial stage, the first layer 10 can be formed by a composite sheet including the sheet materials 15A and 15B with protrusions/depressions and the additional sheet material 17 that exerts the water pressure resistant function at the initial stage as shown in FIGS. 5(a) and 5(c). Then, the additional sheet material 17 is placed on a surface that faces the second layer (the absorptive layer) of the sheet materials 15A and 15B with protrusions/depressions. The first layer 10 may be formed by a composite sheet material of three or more sheet materials by using more additional sheet materials.

A hydrophobic ointment base such as a white petrolatum or a liquid paraffin (Plastibase (registered trademark)) may be applied on the surface material (sheet material) of the first layer 10 for the purpose of avoiding a stimulus from friction with the wound and for the purpose of improving the adhesion with the wound surface.

Moreover, a medicine for promoting the wound healing may be applied on the surface material (sheet material) of the first layer 10 or the surface material may be impregnated with such a medicine. The medicine may be, for example, Trafermin (commercially available under the name "Fiblast Spray 250" from KAKEN Pharmaceutical CO., LTD.), or the like, which is known to promote skin growth.

Referring to FIGS. 1(a) and 1(b), the second layer 20 or the absorptive layer 20 absorbs the exudate, which has exuded from the wound site and passed through the first layer 10. The material of the second layer 20 may be a material capable of absorbing and holding a liquid therein such as a hydrophilized non-woven fabric, a flocculated pulp, an air-laid non-woven fabric (air-laid pulp), or the like. The second layer 20 or the absorptive layer 20 is preferably made of a non-woven fabric that has been made into a sheet through interfiber bonding with a binder (adhesive agent) or compression so that lint or an absorbent 22 to be described later will not come off the cut end of the dressing 1 when it is cut. Particularly, an air-laid non-woven fabric is preferred.

An air-laid non-woven fabric is a non-woven fabric obtained by separating material pulp fibers or staple fibers uniformly in the air and letting the fibers deposit on a rotary porous cylinder or a moving screen belt while spraying a water-soluble adhesive agent thereto to bond the fibers together. It is preferred to use an air-laid non-woven fabric whose primary component is pulp fibers so as to facilitate the absorption of the exudate. The production method of such a non-woven fabric may be the Dan-Web method, the Honshu method, or the like.

The air-laid non-woven fabric may include super water-absorbing polymer powder (absorbent). In the air-laid non-woven fabric, components of the non-woven fabric, such as the fibers thereof, are bonded together with an adhesive agent under a pressure, whereby it is unlikely that the super water-absorbing polymer powder or the fluff pulp will come off when, for example, a dressing is cut out of the air-laid non-woven fabric.

Alternatively, the air-laid non-woven fabric may include a water-insoluble continuous fiber.

A continuous fiber refers to a chemical fiber or a natural fiber having a greater fiber length (e.g., 5 mm or more) than that of a pulp fiber. Specifically, the continuous fiber may be a water-insoluble fiber, including a regenerated fiber such as a viscose rayon or a solvent-spun rayon, a semi-synthetic fiber such as a cellulose acetate, a synthetic fiber such as a polyamide fiber, e.g., Nylon 6 or Nylon 66 (registered trademarks), a polyester fiber, e.g., a polyethylene terephthalate, a polyethylene fiber and a polypropylene fiber, and a natural fiber such as cotton and hemp. Particularly, it is preferred to use a synthetic fiber, which suffers only a little decrease in strength when being wet.

Moreover, the air-laid non-woven fabric may include a binder fiber. A binder fiber refers to a fiber capable of becoming adhesive as the whole or part of the fiber undergoes state transitions, i.e., fusion and solidification, depending on the temperature condition. Specifically, the binder fiber may be a wholly fusible fiber formed solely by a low-melting resin such as a polyester resin or a polyamide resin, or a polyolefin resin, or may be a sheath-core type composite fiber or a side-by-side type composite fiber made of two resins having different melting points, e.g., polyethylene resin/polypropylene resin or low-melting polyester resin/polypropylene resin.

Alternatively, the second layer 20 or the absorptive layer 20 may be a sheet-shaped composite. The sheet-shaped composite is obtained by, for example, impregnating a non-woven fabric with an acrylic acid monomer and then subjecting it to polymerization and cross-linking. Another example of the sheet-shaped composite can be obtained by pouring a dispersion liquid over a sheet-shaped support such as a non-woven fabric and then drying the dispersion liquid, the dispersion liquid being obtained by dispersing a highly hydratable fibrous substance (e.g., microfibril, etc.) and a water-swellable solid substance (e.g., any of various polysaccharides, a flocculent, a super absorbing polymer (SAP), etc.) in a mixed solvent of an organic catalyst and water.

As the absorptive layer (the second layer) 20 absorbs the exudate, the hydrogen bond between pulp fibers of the air-laid non-woven fabric is broken and the water-soluble binder dissolves to thereby reduce the interfiber bond when being wet. Particularly, in a case where the air-laid non-woven fabric contains a super water-absorbing polymer, the entanglement and bonding between constituent fibers are physically broken due to a decrease in strength caused by the gelation of the super water-absorbing polymer and an increase in the volume of the resin caused by the gelation, whereby there is a significant decrease in the wet strength of the air-laid non-woven fabric.

However, an air-laid non-woven fabric, because of its inclusion of at least a water-insoluble continuous fiber and a binder fiber, is capable of maintaining the minimum interfiber bond required, whereby it is possible to suppress the decrease in wet strength of the air-laid non-woven fabric. Therefore, it is possible to suppress the air-laid non-woven fabric from being peeled off the water-absorbing layer of the dressing due to a decrease in strength of the air-laid non-woven fabric, which is likely to occur after absorbing the exudate. Thus, the dressing can be peeled off the wound surface easily and cleanly.

The air-laid non-woven fabric of the second layer 20 or the absorptive layer 20 may be softened through perforation. "Perforation" as used herein refers to a process of making a large number of pores in a non-woven fabric. Since fibers of an air-laid non-woven fabric are bonded together with an adhesive agent, the cloth is likely to have a high degree of stiffness and thus poor softness. However, making a large number of pores in the non-woven fabric softens the non-woven fabric, which will then better conform to the skin surface. Moreover, a non-woven fabric subjected to such a process can absorb the exudate through the pores, whereby once it starts absorbing the exudate, the water-absorbing speed increases.

The cross-sectional shape of pores formed through perforation is not limited to any particular shape. Moreover, the pores may or may not completely penetrate the air-laid non-woven fabric.

In order to further enhance the ability to absorb and hold the exudate, the second layer 20 may include the absorbent 22 as shown in FIG. 1(b). An absorbent refers to a material that, when contacted by a liquid, quickly absorbs the liquid and swells to be a gel. The absorbent is preferably a so-called "super water-absorbing polymer (SAP)" such as a polyacrylic acid SAP, a starch-based SAP, a carboxymethyl cellulose SAP, a polyvinyl alcohol SAP and a polyethylene oxide SAP, a natural polysaccharide having a high water-absorbing capacity such as alginic acid or dextran, or the like. The absorbent 22 may be a fibrous absorbent, as well as a powder absorbent or a granular absorbent.

Moreover, by processing the absorbent 22 with a calcium salt, the absorbent 22 can be provided with a hemostatic effect for the wound surface.

The second layer 20 may be given some elasticity by, for example, making intermittent cuts (forming pores through perforation) in the material of the second layer 20.

The third layer (the impermeable layer) 30 is provided so that the second layer 20 is sandwiched between the third layer 30 and the first layer 10. In other words, the second layer 20 is provided between the first layer 10 and the third layer 30. The material of the third layer 30 is a material impermeable to liquid, and may be, for example, a film of an olefin resin (polyethylene, polypropylene, etc.), a polyester resin, a nylon resin, or the like. The material of the third layer 30 may be an elastic film such as a polyurethane resin, or the like. In a case where the three layers 10, 20 and 30 are all elastic, the dressing 1 gives an improved fit to the skin because of the elasticity of the dressing 1.

A colored film or a film with a design thereon may be used as the sheet material of the third layer 30.

The use of a colored film or a film with a design thereon as the third layer 30 provides various advantages. For example, if a skin-colored film is used, it is possible to reduce the awkwardness due to the difference between the color of the wound site and that of the skin in other areas. The use of a differently-colored film or a film with a design thereon gives an aesthetic appearance to the dressing.

The film material of the third layer 30 or the impermeable layer 30 may be colored. This makes the front and back sides more easily discernible from each other. In other words, the side of the dressing can be discerned at a glance. The use of a skin-colored film material makes the dressing less conspicuous.

The film material of the third layer 30 or the impermeable layer 30 may be transparent. Then, the amount of exudate that has been absorbed by the second layer 20 or the absorptive layer 20 can be visually checked, whereby it is possible to more easily determine when to replace the dressing.

Figure 2:
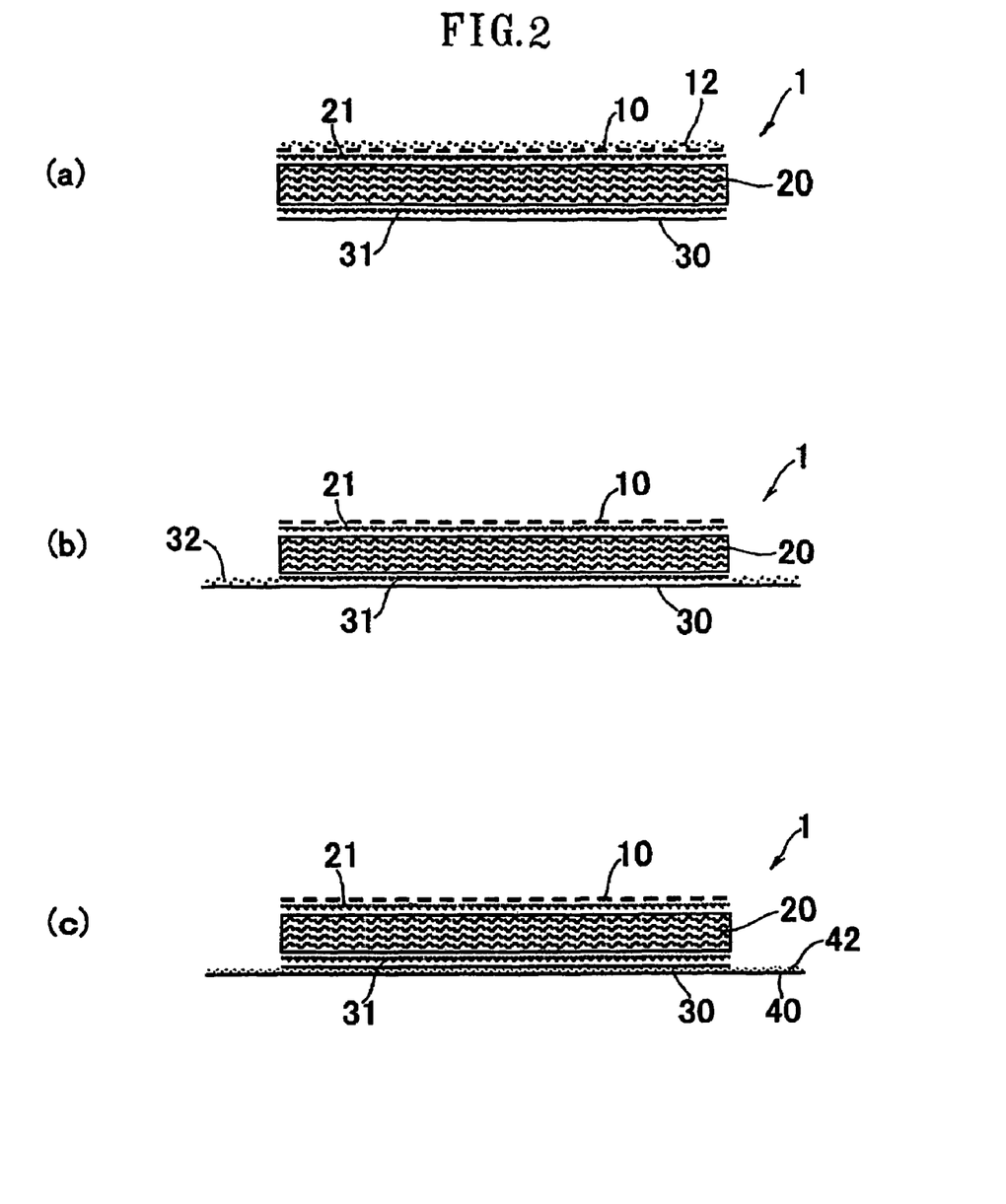

The dressing 1 may be provided with one or more adhesive members 12, 32, 42, as shown in FIGS. 2(a) to 2(c). An adhesive member refers to a member that is capable of securing the dressing while keeping such a condition that the dressing can easily be peeled off. Specifically, the adhesive member may be an acrylic or silicon adhesive material, or the like, which is low-irritant and less likely to cause a rash on the skin. The adhesive member 12 may be applied on the surface material of the first layer 10 on the wound surface side (the surface on which the dressing is applied on the skin) to such a degree that it will not hamper the liquid permeability of the first layer 10. The dressing 1 of this type is easy to handle. Specifically, the dressing 1 can easily be secured on the wound surface, and the dressing can be freely cut into a piece of a size according to the size of the wound.

As shown in FIG. 2(b), the anti-leak sheet 30 of the third layer may be larger than the first and second layers 10 and 20, with the adhesive material 32 being applied on the wound surface side of the anti-leak sheet 30.

Alternatively, as shown in FIG. 2(c), the dressing 1 may further include a sheet with the adhesive material 42 applied thereon, as a fourth layer 40, layered on the outer side of the anti-leak sheet 30. Moreover, the dressing 1 may include a piece of release paper or film for protecting the adhesive member until when the dressing is used.

Figure 3:
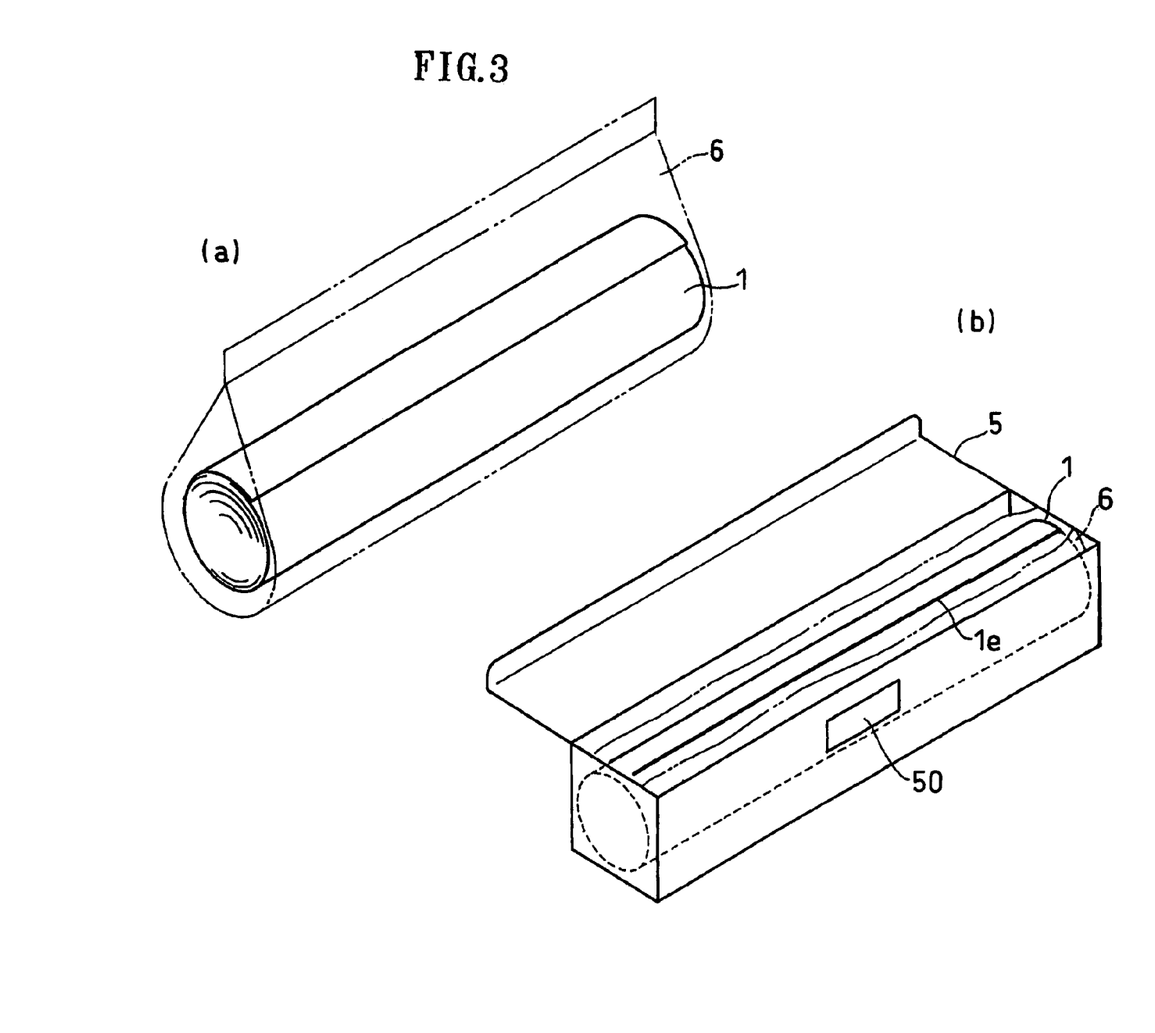

As shown in FIGS. 3(a) and 3(b), the dressing 1 may be rolled up into a roll form. The dressing 1 being in a roll or sheet form may, be packaged in a resin film (an example of a package) 6, or the like.

If the dressing 1 is provided in a sheet form, a plurality of dressings 1 may be packaged together in a resin film. Packaging the dressing or dressings 1 in a resin film enables a reliable control of the sterilization validation. The resin film may be of a material that can withstand a sterilization process such as an ethylene oxide gas sterilization, an electron beam sterilization, a gamma ray sterilization, or the like.

The dressing being in a roll or sheet form can be cut into a piece of an intended size before use.

Alternatively, the dressing being in a roll or sheet form may be accommodated and packaged in a box 5. In this case, the dressing 1 may further be accommodated in the film 6. The dressing 1 being in a roll form may be held rotatably by supporting the circumferential surface of the dressing 1 with the inner surface of the box 5, or by rotatably supporting the core of the roll with the box 5. When the box 5 is opened and an end 1e of the roll is pulled out, the roll rotates and a part or whole of the dressing 1 can be taken out. This facilitates the handling and storage of the dressing 1.

The box 5 may be provided with an area 50 in which various diagnostic information can be written down for the purpose of making it easier to check the identification and medical treatment history of a patient.

INDUSTRIAL APPLICABILITY

The dressing of the present invention can be directly applied on the wound surface for medical treatment of a wound such as a burn, a decubitus, a contusion, an excoriation, an ulcer, or an incision wound from a surgery. The dressing of the present invention can also be used as a secondary dressing for covering and securing a wound dressing, a piece of gauze, or the like, and for preventing the leakage of blood, exudate, etc., therethrough.

What is claimed is:

1. A wound dressing, comprising a first layer including a hydrophobic sheet that exerts a water pressure resistant function at an initial stage, wherein the hydrophobic sheet comprises a permeable, non-woven fabric; a second layer including an absorptive material, that exerts a function of absorbing an exudate, which has exuded from the wound site and passed through the first layer; and a third layer including a sheet impermeable to liquid, wherein the initial stage is after the dressing is applied to the wound site and the exudate is held on the wound surface by a waterproof effect of the hydrophobic sheet that exerts the water pressure resistant function, this forms a closed space thereby preserving a wet environment therein.

2. A wound dressing adapted to be applied on a wound site so as to cover the wound site, comprising a first layer, an absorptive layer and an impermeable layer, the layers being integrally stacked together so that the absorptive layer is sandwiched between the first layer and the impermeable layer, wherein:

the first layer has hydrophobicity and comprises a permeable, non-woven fabric and exerts a water pressure resistant function at an initial stage;

the absorptive layer exerts a function of absorbing an exudate, which has exuded from the wound site and passed through the first layer; and the impermeable layer is impermeable to liquid, thereby preventing leakage of the exudates;

wherein the initial stage is after the dressing is applied to the wound site and the exudate is held on the wound surface by a waterproof effect of the hydrophobic sheet that exerts the water pressure resistant function, this forms a closed space thereby preserving a wet environment therein.

3. A wound dressing according to claim 2, wherein an air permeability of the first layer measured according to JIS L 1096 is 20 $cm^3/cm^2 \cdot s$ to 2000 $cm^3/cm^2 \cdot s$ and a water repellency score of the first layer measured according to JIS L 1092 is 3 points or more.

4. A wound dressing according to claim 2, wherein the first layer includes a sheet, an air permeability of the sheet measured according to JIS L 1096 being 20 $cm^3/cm^2 \cdot s$ to 2000 $cm^3/cm^2 \cdot s$ and a water repellency score of the sheet measured according to JIS L 1092 being 3 points or more.

5. A wound dressing according to claim 4, wherein, at the initial stage the amount of the exudate is small, and at a later stage when a pressure in the closed space formed between the wound surface and the sheet is increased, the sheet exerting the water pressure resistant function at the initial stage allows an excessive amount of the exudate to be discharged into the second layer through the sheet.

6. A wound dressing according to claim 4, wherein the first layer includes a porous sheet, a depth of pores in the porous sheet is set to be about 100 µm to 2000 µm, a pore ratio of the porous sheet is set to be 5% to 50%, and the porous sheet is placed on a contact surface facing the wound site.

7. A wound dressing according to claim 3, wherein, at the initial stage the amount of the exudate is small, and at a later stage when a pressure in the closed space formed between the wound surface and the first layer is increased, the first layer exerting the water pressure resistant function at the initial stage allows an excessive amount of the exudate to be discharged into the second layer through the first layer.

8. A wound dressing according to claim 7, wherein the first layer includes a porous sheet, a depth of pores in the porous sheet is set to be about 100 µm to 2000 µm, a pore ratio of the porous sheet is set to be 5% to 50%, and the porous sheet is placed on a contact surface facing the wound site.

9. A wound dressing according to claim 3, wherein the first layer includes a porous sheet, a depth of pores in the porous sheet is set to be about 100 µm to 2000 µm, a pore ratio of the porous sheet is set to be 5% to 50%, and the porous sheet is placed on a contact surface facing the wound site.

10. A wound dressing according to claim 2, wherein, at the initial stage the amount of the exudate is small, and at a later stage when a pressure in the closed space formed between the wound surface and the first layer is increased, the first layer exerting the water pressure resistant function at the initial stage allows an excessive amount of the exudate to be discharged into the second layer through the first layer.

11. A wound dressing according to claim 10, wherein the first layer includes a porous sheet, a depth of pores in the porous sheet is set to be about 100 µm to 2000 µm, a pore ratio of the porous sheet is set to be 5% to 50%, and the porous sheet is placed on a contact surface facing the wound site.

12. A wound dressing according to claim 2, wherein a contact surface of the first layer that faces the wound site has a surface configuration with asperity.

13. A wound dressing according to claim 2, wherein the first layer includes a porous sheet, a depth of pores in the porous sheet is set to be about 100 µm to 2000 µm, a pore ratio of the porous sheet is set to be 5% to 50%, and the porous sheet is placed on a contact surface facing the wound site.

14. A wound dressing according to claim 2, further comprising an absorbent in the absorptive layer.

15. A wound dressing according to claim 2, wherein the absorptive layer is formed by an air-laid non-woven fabric.

16. A wound dressing according to claim 15, wherein the air-laid non-woven fabric includes at least one of an absorbent, a water-insoluble continuous fiber and a binder fiber.

17. A wound dressing according to claim 15, wherein the air-laid non-woven fabric is perforated.

18. A wound dressing according to claim 2, wherein the impermeable layer includes a colored and/or transparent material.

19. A wound dressing according to claim 2, wherein the wound dressing is rolled up into a roll form.

20. A wound dressing kit, comprising a wound dressing according to claim 2, and a package accommodating the wound dressing.

21. A wound dressing according to claim 2 wherein the non-woven fabric comprises a meltblown fabric or a flash-spun fabric.

* * * * *